United States Patent [19]

Bond et al.

[11] 4,011,748
[45] Mar. 15, 1977

[54] METHOD AND APPARATUS FOR ACOUSTIC AND OPTICAL SCANNING OF AN OBJECT

[75] Inventors: Walter L. Bond, Los Altos, Calif.; Rudolf Kompfner, Oxford, England; Ross A. Lemons, Mountain View, Calif.

[73] Assignee: The Board of Trustees of Leland Stanford Junior University, Stanford, Calif.

[22] Filed: Sept. 18, 1975

[21] Appl. No.: 614,440

[52] U.S. Cl. .............................. 73/67.6; 73/67.8 S; 340/5 MP

[51] Int. Cl.² ...................................... G01N 29/04

[58] Field of Search .......... 73/67.5 R, 67.5 H, 67.6, 73/67.7, 67.8 R, 67.8 S, 67.9; 340/5 H, 5 MP

[56] References Cited

UNITED STATES PATENTS

| | | | |
|---|---|---|---|
| 2,919,574 | 1/1960 | Fotland | 73/67.6 |
| 3,024,644 | 3/1962 | Fry et al. | 73/67.5 R |
| 3,448,606 | 6/1969 | Flaherty et al. | 73/67.8 S |
| 3,686,932 | 8/1972 | Ries et al. | 73/67.8 R |
| 3,774,717 | 11/1973 | Chodorow | 73/67.7 X |
| 3,790,281 | 2/1974 | Kessler et al. | 73/67.5 R X |

OTHER PUBLICATIONS

R. A. Lemons et al, Acoustic Microscope–Scanning Version, Applied Physics Letters, vol. 24, No. 4, Feb. 15, 1974, pp. 163–165.

*Primary Examiner*—Richard C. Queisser
*Assistant Examiner*—John P. Beauchamp
*Attorney, Agent, or Firm*—Flehr, Hohbach, Test, Albritton & Herbert

[57] ABSTRACT

A microscope for scanning an object with light and acoustic waves and producing both acoustic and optical images thereof. The microscope includes optical and acoustic lenses that focus both the light and acoustic waves on substantially the same point on the object. In one portion of the microscope the acoustic waves and light propagate coextensively through the same medium. The apparatus generates a simultaneous presentation of both acoustic and optical images formed by the microscope.

33 Claims, 8 Drawing Figures

METHOD AND APPARATUS FOR ACOUSTIC AND OPTICAL SCANNING OF AN OBJECT

GOVERNMENT CONTRACT

The invention herein described was made in the course of or under a contract or subcontract thereunder, (or grant) with the Department of the Navy.

BACKGROUND OF THE INVENTION

1. Field of the Invention

This invention generally relates to acoustic imaging systems and, more particularly, to acoustic scanning apparatus.

2. Description of the Prior Art

U.S. Pat. Application filed on Feb. 15, 1974, bearing Ser. No. 442,782, entitled "Scanning Acoustic Microscope," by Mr. Ross Lemons et al., now abandoned, discloses a microscope for scanning an object with ultrasonic acoustic waves. The microscope focuses a high frequency acoustic plane wave with an acoustic lens and scans an object located at the focal plane of the lens. The acoustic waves modulated by the object are recollimated by a second acoustic lens and detected with a piezoelectric transducer. The detected acoustic signal is applied to an oscilloscope that provides a visual display of the acoustic image of the object.

OBJECTS AND SUMMARY OF THE INVENTION

An object of the present invention is to record and display both the acoustic and optical images of an object so that the correspondence between the two images can be visualized. In the present invention, the simultaneous presence of an observable feature on the object seen in both of the images as well as the presence of an observable feature in only one of the images can provide clues to the structure of the object which each image alone cannot give to the operator.

An additional object of the present invention is to permit the operator of the microscope to visually observe the object being acoustically imaged through an optical lens system. The present invention permits the operator to visually view the object and to center an interesting area on the object within the scanning range of the microscope.

These and other objects described herein are achieved by a microscope comprising an optical lens system for focusing light on the focal plane of the microscope and an acoustic lens system for focusing acoustic waves on the same focal plane. The acoustic waves and the light are modulated by the object either by reflection or transmission through the object. The modulated acoustic waves and modulated light are converted into electrical signals that modulate the intensity of cathode ray tubes. The object being scanned is moved through the focal plane in a raster pattern synchronized to the raster scan of the cathode ray tubes. Thus, one cathode ray tube has a visual output corresponding to the optical image of the object and another cathode ray tube, the acoustic image.

Additional objects and features of the present invention will appear from the description that follows wherein the preferred embodiments have been set forth in detail in conjunction with the accompanying drawings.

DESCRIPTION OF THE PREFERRED EMBODIMENTS

Figure 1:
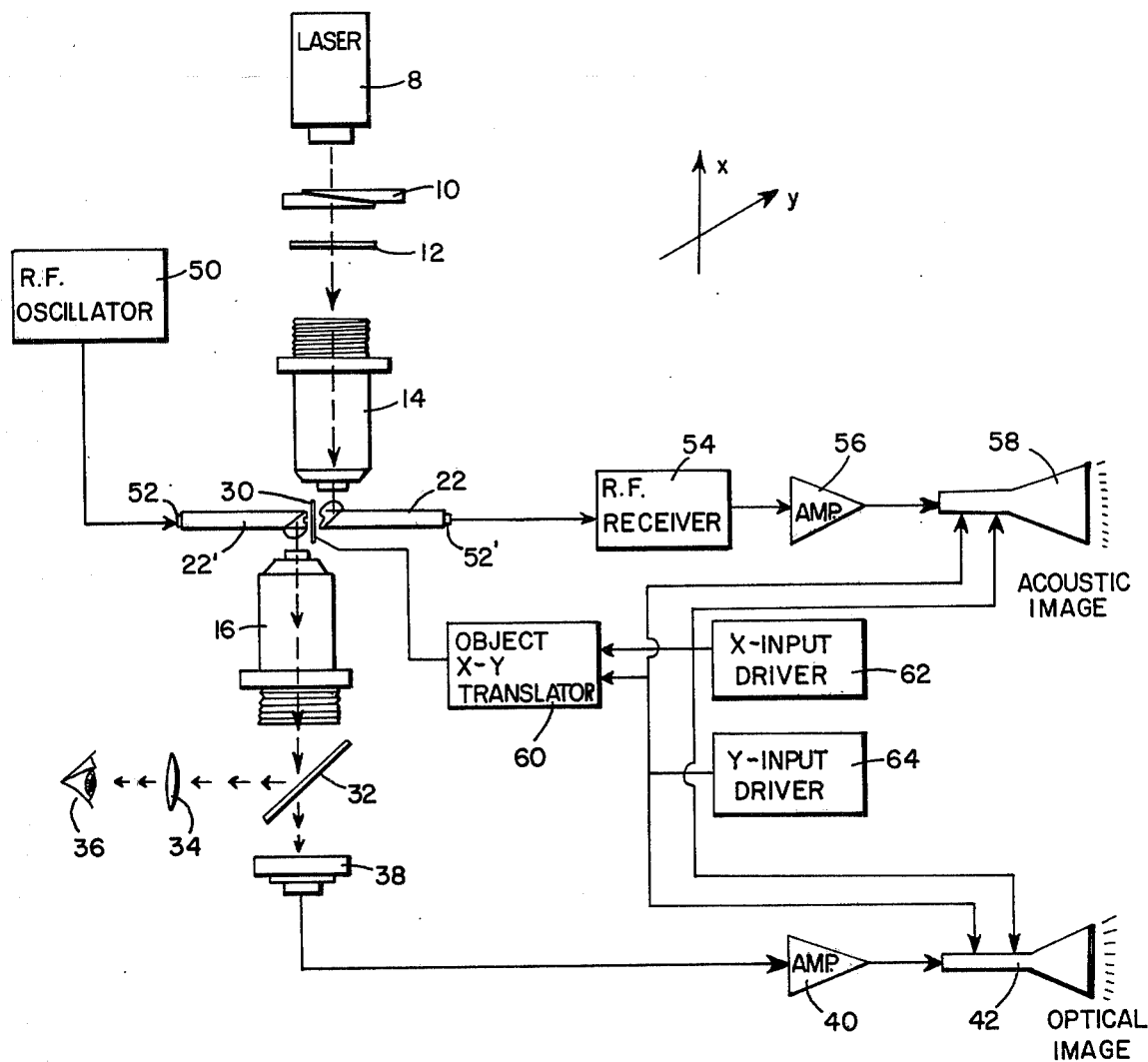
FIG. 1 is a block diagram of an acoustic and optical scanning microscope according to the present invention.
Figure 6:
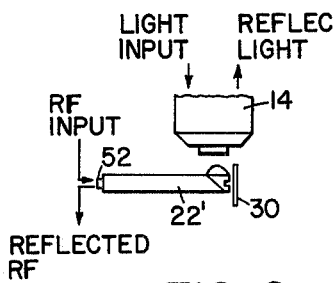
FIG. 6 is a diagrammatic side elevation, partially cut away, of the optical and acoustic lenses of the present invention. In this figure both the light and the acoustic waves are reflected from the object.
Figure 7:
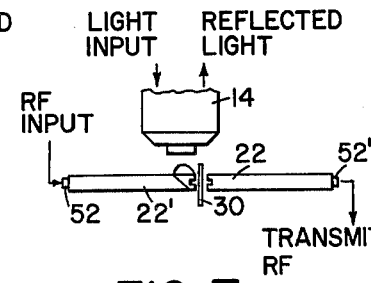
FIG. 7 is a diagrammatic side elevation, partially cut away, of the optical and acoustic lenses of the present invention. In this figure the light is reflected and the acoustic waves are transmitted through the object.
Figure 8:
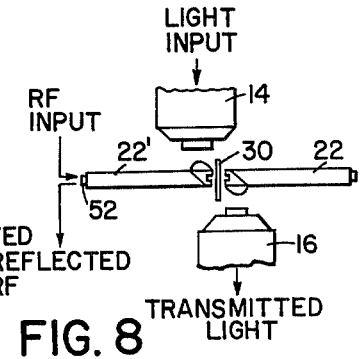
FIG. 8 is a diagrammatic side elevation, partially cut away, of the optical and acoustic lenses of the present invention. In this figure the light is transmitted through and the acoustic waves are reflected from the object.

FIG. 1 is a complete block diagram of the acoustic and optical scanning microscope according to one embodiment of the present invention. The microscope comprises an optical lens subsystem which is described first and an acoustic lens subsystem described thereafter. Both lens subsystems focus on the same point on the object being scanned. The object is moved through the focus by an object translator in a raster pattern synchronized with the raster scan of the output oscilloscopes. The modulation of each beam by the object appears on the respective output oscilloscope as an intensity variation or in contrast with respect to the other areas scanned by the microscope.

In the optical lens subsystem light is provided by either a conventional incandescent light source (not shown) or a laser 8. In the preferred embodiment a laser is used because it provides an accurately collimated light beam that can be brought to a small, sharp, focal point. A suitable laser for the present invention is a conventional helium neon laser having an output of approximately two milliwatts. The light beam from the laser 8 is directed into a conventional neutral intensity control 10. The intensity control regulates the intensity of the light beam so that the laser does not burn the object in the microscope. The light thereafter passes through an adjustable iris 12 for controlling the width of the light beam and the resolution of the optical system.

Figure 2:
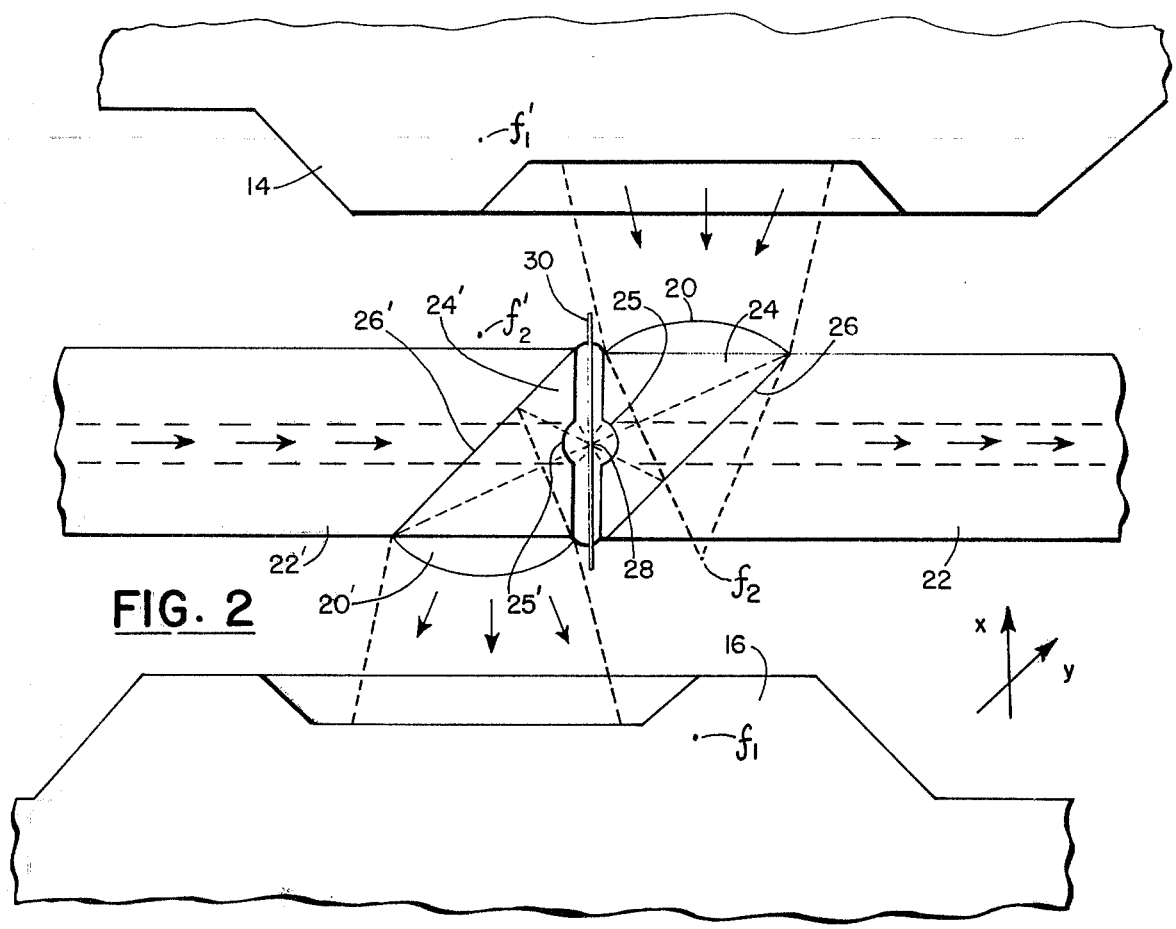
FIG. 2 is a diagrammatic side elevation, partially cut away, of the acoustic and optical lenses in the microscope illustrated in FIG. 1. In this figure the light is reflected within the acoustic propagating medium onto the focal plane.

Referring to FIGS. 1 and 2, the light passing through the iris 12 is directed into the first lens element 14 of the optical lens system. In the preferred embodiment this first lens element is a conventional microscope objective lens. A microscope objective is used because it provides very accurate focusing of a collimated light beam. The light passing through the objective 14 is focused at point $f_1$ in FIG. 2.

Referring to FIG. 2, the light leaving the objective lens 14 passes through a plano-convex lens 20 located at one end of an acoustic propagating medium 22 and focuses the beam at the point $f_2$, FIG. 2. The plano-convex lens is aplanatic to the focal point 28 hereinafter described. In this embodiment the acoustic propagating medium is a rod and both the plano-convex lens and the rod are fabricated from a light transmitting material such as YAG, or fused quartz. The plano-convex lenses can be fabricated as integral parts of the rods or the lenses can be separately fabricated and attached during the assembly of the microscope. When the plano-convex lenses are separately fabricated, rectangular rods are used to provide a lens mounting surface and the lenses are attached to the rods using a material such as Canada balsam that matches the refraction index for light.

The light next passes through a prism 24 fabricated from the same material as the propagating medium. The use of the same material for the lenses 20, rods 22 and prisms 24 insures that each component has the same index of refraction.

The interface (FIG. 2) between the prism 24 and the rod 22 forms a light reflecting surface 26 that directs the light to the focal plane 28. As hereinafter described, the interface passes acoustic energy without distortion. In the preferred embodiment the light reflecting surface is a thin layer of gallium. Gallium is a metallic element that is highly reflective to light, and gallium also provides an acoustic match between the prism and the rod so that acoustic energy can pass directly through the interface without substantial scattering or reflection. The optical reflecting surface can also be fabricated by depositing a thin layer of gold on the interface or forming an indium thermal compression bond between the rod and the prism.

The elements of the optical lens system hereinbefore described are complemented by an identical system of identically fabricated and mounted elements. The corresponding elements are identified by primed numbers.

After passing through the focal plane 28 (FIG. 2), the light is directed by the prism 24', the reflecting surface 26', and the plano-convex lens 20' into a second microscope objective lens 16. All of these optical elements are identical to the elements hereinbefore described. The light passes through the second objective and is incident on an optical beam splitter 32 (FIG. 1). The unreflected portion of the light passes through the beam splitter and is incident on a photodetector 38. The photodetector converts the incident light into a corresponding electrical signal. In the preferred embodiment the photodetector can be either a conventional silicon photodiode detector or a photomultiplier. The output signal from the photodetector is amplified by an amplifier 40 and is used to modulate the intensity of an oscilloscope 42.

In the preferred embodiment the beam splitter is a semi-silvered glass plane that reflects a portion of the light out of the microscope for direct viewing. For the purpose of direct observation, the illumination provided by the light source is spread over a finite area of the object 30 either by defocusing the microscope objective 14 or by including an auxillary lens (not shown) between the light source and the objective 14. An incandescent light source is preferred for direct observation. If the laser 8 is used, its output power must be attenuated sufficiently with the intensity control 10 for safe viewing by the operator 36.

ACOUSTIC SUBSYSTEM

The other major subsystem of the scanning microscope comprises the components that handle the acoustic waves. Referring to FIGS. 1 and 2, the acoustic wave subsystem includes a radio frequency oscillator 50 operating in a frequency range of between 200 and 1500 MHz. The output of the oscillator is connected to a transducer 52 that converts the high frequency output of the oscillator into acoustic wave. In the preferred embodiment the transducer is a zinc oxide layer deposited on one end of one of the acoustic wave propagating media 22'. The acoustic propagating media in the preferred embodiment are YAG rods having a rectangular cross section. The cross section is rectangular in order to provide a flat mounting surface for the plano-convex lenses.

Referring to FIG. 2, the acoustic waves produced by the transducer propagate through the rod 22' and pass through the optical reflecting surface 26' without substantial acoustic reflection. The acoustic waves are thereafter focused on the focal plane 28 by the acoustic lens 25' and pass through the focal plane and are refracted into a beam by an opposing acoustic lens 25. It should be noted that in the area between the two reflecting surfaces 26, 26' the light and the acoustic waves are coextensive because each beam has the same axis of propagation and simultaneously travels through the same volume of material.

The object 30 being scanned by the microscope is positioned between the acoustic lenses 25, 25'. The volume between the two rods 22, 22' and the object is filled with a fluid that promotes the propagation of acoustic waves across the gap. In the preferred embodiment the gap between the rods is filled with water and, since the gap is so small, the water remains in place by its own surface tension.

The details of the construction and operation of the acoustic wave subsystem of the present invention are further described in Lemons et al. U.S. Pat. Application, Ser. No. 442,782 entitled "Scanning Acoustic Microscope" hereinbefore described.

The object 30 is moved through the focal plane 28 in a raster pattern by an X–Y object translator 60. The translator is driven along the X axis by an X input driver 62 and along the Y axis by a Y input driver 64. The output of the X input driver is also connected to the horizontal input to the oscilloscopes 42, 58 and the output of the Y input driver 64 is connected to the vertical input of the oscilloscopes. The motion of the object is thereby synchronized with the raster scan on the oscilloscopes. The details of construction and operation of the object translator and the X and Y input drivers are further disclosed in Lemons et al. U.S. Pat. Application Ser. No. 442,782 entitled "Scanning Acoustic Microscope" hereinbefore described.

Figure 3:
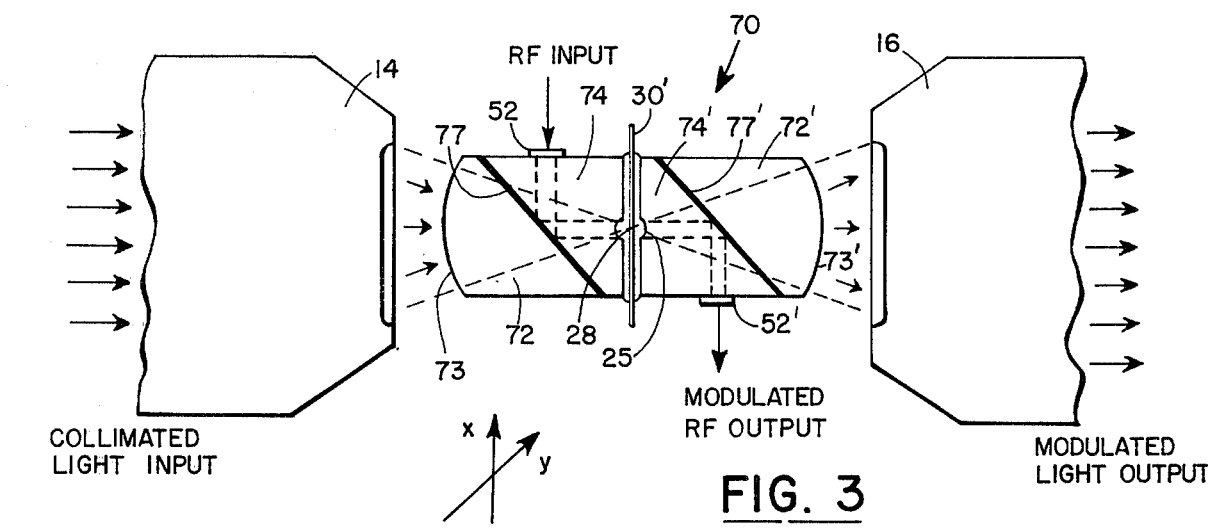
FIG. 3 is a diagrammatic side elevation, partially cut away, of the optical and the acoustic lenses of an alternative embodiment of the present invention. In this figure the acoustic waves are reflected in the optical propagating medium onto the focal plane.

It should be appreciated the FIGS. 1, 2 and 3 do not illustrate the mechanical staging required to bring both the acoustic and optical subsystems into precise alignment and to place their respective foci in coincident relationship. Both the objective lenses 14, 16 and the acoustic propagating rods 22, 22' require three dimensional mechanical adjustment stages. These adjustment stages are commercially available and for brevity have not been described.

OPERATION

The scanning microscope illustrated in FIGS. 1 and 2 includes two, independently operable, subsystems. In the optical subsystem collimated light is generated from the laser 8 (FIG. 1) and is filtered by an intensity control 10 to reduce its power. The light passes through an adjustable iris 12 and is focused by a microscope objective 14 on the focal point $f_1$ (FIG. 2). The optical subsystem is brought into alignment by a plurality of mechanical stages (not shown).

As illustrated in FIG. 2, the light passing out of the objective lens 14 is refracted by the plano-convex lens 20 to a focal point F2 and is reflected by the interface 26 of the rod 22 onto the optical focal plane 28. The light rays pass throught the object 30 and are modulated by its structure. The modulation of the light by different areas of the object generates the optical image and is observed as light and dark areas on the oscilloscope display.

After being transmitted through the object, the light is refracted by the plano-convex lens 20' into the second objective lens 16. The light next leaves the objective 16 and is both reflected and passed through the beam splitter 32. The light reflected by the beam splitter is focused by the lens 34 and observed by the operator 36. The light passing through the beam splitter is converted into an electrical output signal by the photodetector 38. The electrical signal from the photodetector is amplified and used to modulate the intensity of the oscilloscope 42.

The other, independently operable subsystem of the scanning microscope is the acoustic wave subsystem. This subsystem operates by generating acoustic waves in the rod 22' (FIG. 1) using the RF oscillator 50 and the transducer 52. The acoustic waves propagate through the rod and are focused on the focal plane 28 (FIG. 2) by an acoustic lens 25. The interface 26' does not reflect or scatter the acoustic waves. The optical lenses and the acoustic lenses are adjusted by a plurality of mechanical stages (not shown) so that the acoustic focal point is coincident with the optical focal point. The acoustic waves pass through the object 30 and are modulated by its structure in a manner similar to the light beam hereinbefore described.

After passing through the object 30, the acoustic waves are refracted by the acoustic lens 25 (FIG. 2) and pass through the interface 26 without reflection. The acoustic waves are converted into an electrical signal by the transducer 52' and are detected and amplified by the RF receiver 54 and the amplifier 56. The output of the amplifier 56 is used to modulate the intensity of the oscilloscope 58.

The object being scanned by the microscope is translated in a plane orthogonal to the axis of propagation of the acoustic waves and in a raster pattern synchronized to the scan raster of the oscilloscopes 42, 58. The object is translated by the object X–Y translator 60 driven by the X and Y input drivers 62, 64.

The visual output of the oscilloscope 42 (FIG. 1) is a presentation representing the point by point modulation of the beam of light transmitted through the object 30 as the object is translated through the focal point. The optical image of the object is a plurality of light and dark areas on the scope corresponding to the same areas on the object having high and low optical transmittance. The output of the other oscilloscope 58 is a visual image corresponding to the point by point modulation of the acoustic beam transmitted through the object. The acoustic image of the object is likewise a plurality of light and dark areas on the scope corresponding to the same areas on the object having high and low acoustic transmittance.

ALTERNATIVE EMBODIMENT

FIG. 3 illustrates an alternative embodiment of the present invention wherein the optical beam passes directly through the lens system without changing direction, and the acoustic beam is reflected into the axis of propagation of the light. The lens system in this alternative embodiment consists of a lens assembly 70 comprising four elements two of which are located on either side of the object 30 being scanned. The two output elements 72 of the lens system each have a convex optical surface 73 that is aplanatic to the focal point 28 of the acoustic lens 25. The two inner elements 74 (FIG. 3) each contain an acoustic lens 25 that focuses the acoustic waves on the same focal point 28 as the light beam. The two inner and the two outer elements are fabricated from materials having the same optical refractive index. This can be achieved by making both the inner and outer elements from the same material such as YAG. The inner and outer elements are cemented together at the interface 77 by a material that passes light without reflection such as Canada balsam. The interface 77 reflects acoustic waves because of the difference in acoustic impedance between the inner element and the cementing material.

The acoustic waves are introduced into the inner elements 74 (FIG. 3) by a transducer 52 connected to an RF oscillator (not shown). The acoustic waves propagate laterally through the inner element, are reflected by the interface 77 and are focused at the focal plane 28 by the acoustic lens 25. The acoustic waves then pass through the focal plane, are refracted by the second acoustic lens, and reflected onto the other transducer 52'. This transducer converts the acoustic waves into an electrical signal.

The light beam in FIG. 3 passes out of the microscope objective 14 and is focused on point 28 by the lens surface 73. The light passes through the focus of the system, is refracted by the second lens surface 73', and enters the other microscope objective 16. In the space between the two interfaces 77, 77' the light is coextensive with the acoustic waves.

The lens system 70 in FIG. 3 is connected to the components illustrated in FIG. 1 in the same manner as the lens system in FIG. 2. The resulting microscope operates in the same manner as hereinbefore described. Similarly the object 30' is moved in a raster pattern synchronized to the output display.

It is also contemplated to fabricate all of the lens elements 72, 74 in the lens assembly 70 of FIG. 2 from the same material and provide a slight air gap between the inner and outer elements. This air gap at the interface 77 would be sufficient to reflect the acoustic waves and yet would permit a substantial amount of the light to pass across the innerface without reflection.

SECOND ALTERNATIVE EMBODIMENT

Figure 4:
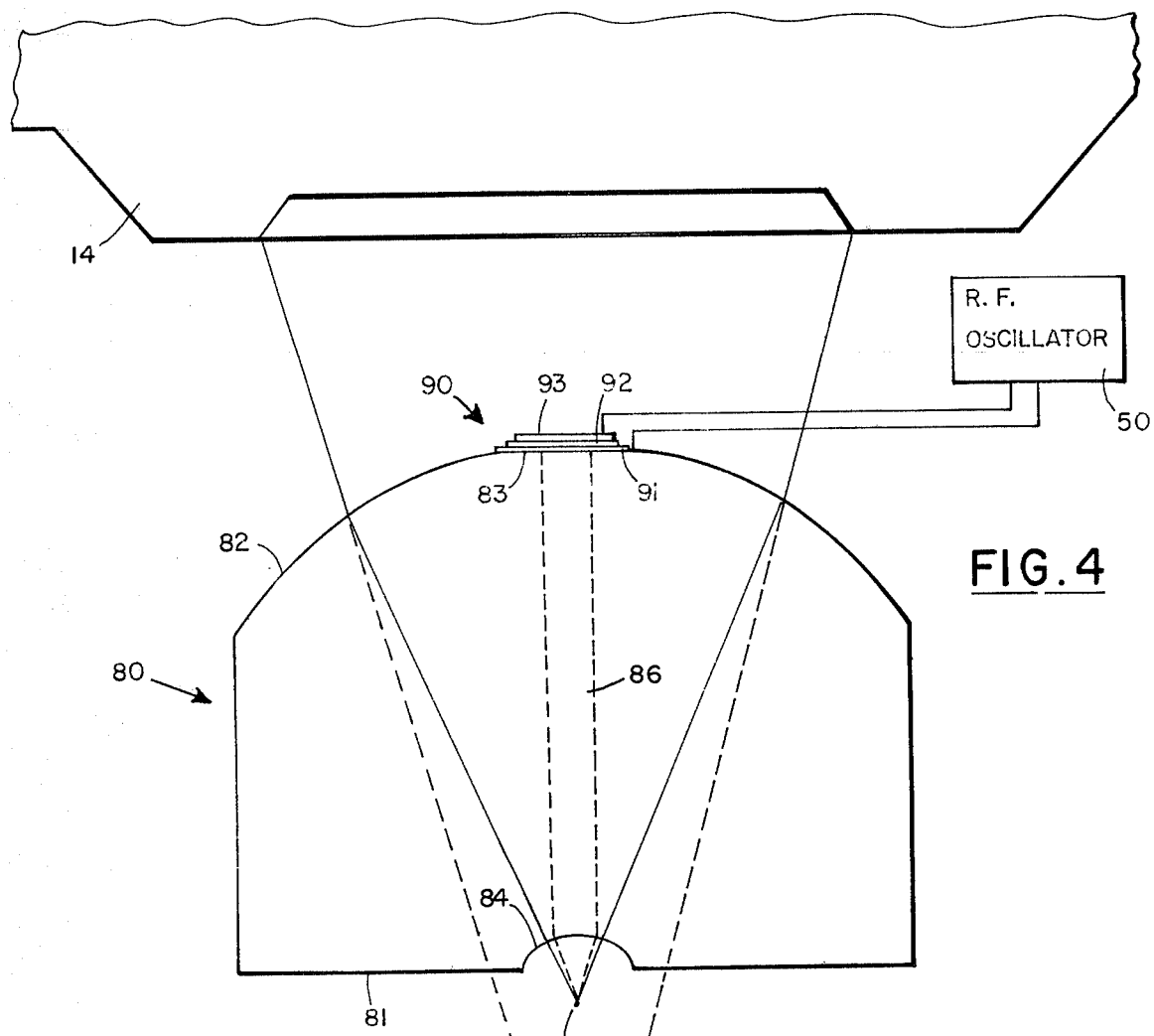
FIG. 4 is a diagrammatic side elevation, partially cut away, of the acoustic and optical lenses of a second alternative embodiment of the present invention. In this figure the acoustic waves and the light coaxially propagate through the lenses and neither wave is reflected out of the lens medium.
Figure 5:
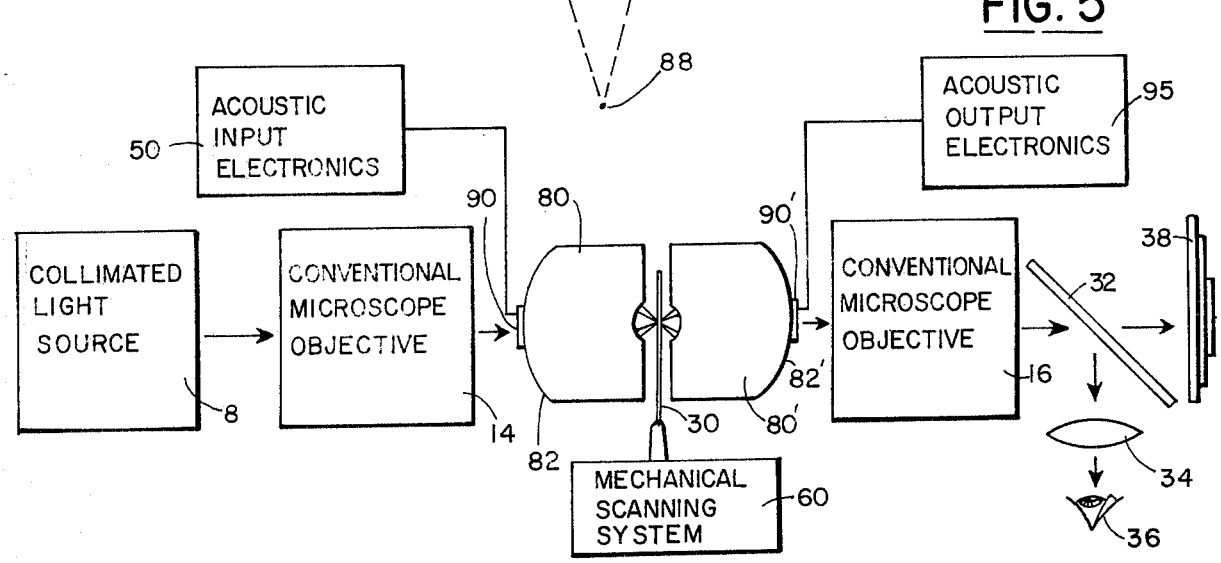
FIG. 5 is a block diagram of an acoustic and optical scanning microscope according to the second alternative embodiment wherein the axis of propagation of light and sound are coincident.

FIGS. 4 and 5 illustrate a second alternative embodiment of the present invention wherein the optical beam and the acoustic beam have coincident coaxial axes of propagation and are coextensive within the lens element. The optical lens subsystem in this second alternative embodiment includes a collimated light source 8, in FIG. 5 that provides an accurately collimated light beam directed toward a conventional microscope objective 14.

The light from the microscope objective 14, FIG. 4 is focused onto a combined acoustic and optical lens element 80. This lens element has the shape of an upright circular cylinder with a spherical surface 82 at one end and a generally planar surface 81 at the other end. The spherical surface 82 has a constant radius of curvature except for a flat surface 83 located at the center of the longitudinal axis of the lens element. The planar surface 81 of the lens element includes a spherical, acoustic lens 84 located opposite the flat plane 83.

The combined acoustic and optical lens element 80 FIG. 4 can be constructed from any material that propagates both acoustic and optical waves. In the preferred embodiment this lens element is fabricated from a material that is isotropic to light so that the velocity of propagation of light is the same in all directions. An isotropic material is used so that the lens elements 80 focuses the light to a sharp point 28. A suitable material for this purpose is YAG. It should be noted that it is not necessary that the lens element 80 be isotropic to sound since the acoustic beam 86 is collimated in the lens element.

The light from the microscope objective 14 is refracted by the spherical surface 82 and brought into a sharp focus at the focal point 28. The light thereafter diverges into a similarly constructed, combined acoustic and optical lens element 80', FIG. 5. This second lens element 80' is constructed and operates in the same manner as the combined lens element 80 hereinbefore described.

The light thereafter passes through a second objective 16, FIG. 5 and is incident on an optical beam splitter 32, FIG. 5. In the preferred embodiment the beam splitter is a semisilvered glass plane that reflects a portion of the light out of the microscope for direct observation. The reflected portion of the light passes through a focusing lens 34 and is observed by the operator 36 in the same manner as hereinbefore described in connection with FIG. 1. The unreflected portion of the light passes through the beam splitter and is incident on a photodetector 38. The photodetector converts the incident light into a corresponding electrical signal. The output signal from the photodetector is amplified and used to modulate the intensity of an oscilloscope (not shown) in the manner hereinbefore described.

The other major subsystem of the second alternative embodiment of the scanning microscope comprises the components that handle the acoustic waves. The acoustic wave subsystem includes a radio frequency oscillator 50 having an output connected to a transducer 90. The transducer is located on the flat plane 83, FIG. 4 of the spherical surface of the combined lens elements 80. The transducer 90 converts the high frequency output of the oscillator 50 into acoustic waves propagating in a collimated beam 86 within the lens element. In the preferred embodiment the transducer includes a counter-electrode 91 deposited on the flat plane 83.

Mounted on top of the counter-electrode is a piezoelectric layer 92 fabricated from zinc oxide. The piezoelectric layer is surmounted by a top-dot electrode 93 that completes the transducer. The counter electrode 91 and the top-dot electrode are connected to the radio frequency oscillator 50.

Referring to FIG. 4, the acoustic waves produced by the transducer 90 propagate through the lens element 80 in a substantially collimated beam 86 and are focused on the focal plane 28 by the acoustic lens 84. It should be noted that in the area between the spherical surface 82 and the focal plane 28 the light and the acoustic waves are coextensive.

The acoustic beam thereafter passes into the corresponding lens element 80', FIG. 5. The acoustic waves pass through the lens element and are refracted into a collimated beam. The acoustic beam is then converted into an electrical signal by the transducer 90'. The electrical signal rom the transducer 90' is amplified and detected by the acoustic output electronics 95. These elecronics correspond to the RF receiver 54 and the amplifier 56, FIG. 1. The output of the electronics 95 is used to modulate the intensity of an oscilloscope (not shown). The object is translated by a mechanical scanning system 60 hereinbefore described.

In operation the second alternative embodiment illustrated in FIGS. 4 and 5 is connected to the output components illustrated in FIG. 1 and described hereinbefore. The entire system operates in the same manner as described in connection with FIGS. 1 and 2 and for brevity need not be repeated. It should be appreciated that the transducer 90, FIG. 4 is not observed in the optical image of the object because the transducer is not located in the focal plane of the microscope. Accordingly the transducer 90 can assume any practical size and is limited only in that a large sized transducer reduces the intensity of the light received from the objective lens 14.

COMMON CHARACTERISTICS

It should be appreciated that each beam in the microscope has its own focusing adjustments and its own focal plane. When both the acoustic and light beams are propagated and refracted to form a focus at the same point, it is these two focal planes that have been brought into coincidence. In FIG. 2 the coincident focal point 28 is achieved by designing the plane-convex lens 20, 20' to be aplanatic to the focal plane of the acoustic lens 25 and by proper positioning of the microscope objectives. In FIG. 3 it is the lens 73 that is aplanatic, and in FIG. 4 it is lens 82. In this context, aplanatic means that the lens introduces no spherical aberration to the light beam. The lenses 22, 73, 82 are chosen to be aplanatic because the acoustic lens 25 only minimally refracts the light passing across its surface. The focal point of the acoustic lens is located very close to the center of curvature of the acoustic lens surface. Consequently, the acoustic lens surface introduces little change in the direction of the light propagating across its surface because the light strikes the curved surface of the acoustic lens at an angle almost normal to the tangent of the surface and propagates very nearly along a radial line between the focal point and the lens surface.

In all of preferred embodiments of the scanning microscope hereinbefore described the object being scanned transmitted both the light and the acoustic waves through its structure. It should be noted, however, that the object can reflect either or both of these beams back through the microscope. In that case, the appropriate detector and oscilloscope are merely moved to the beam's input side of the microscope and the operation of the microscope remains the same. For example, in FIG. 1 if the object reflects light, then the half silvered mirror 32 and the photodetector 38 can be located in the optical path between the laser 8 and the objective 14. If the object reflects acoustic waves, then the electrical input to the R. F. receiver 54 can be taken either from the transducer 52 or from a second transducer (not shown) located proximate to transducer 52. Thus, with a slight rearrangement of components the scanning microscope can operate in the following modes: light transmission/acoustic wave transmission; light reflection/acoustic wave reflection; light transmission/acoustic wave reflection; and light reflection/acoustic wave transmission.

It should also be noted that the output from the microscope need not necessarily be passed directly to the oscilloscope 42, 58. The electrical signals corresponding to the modulated light and acoustic waves and the motion of the object can be processed and/or recorded into other usable formats, allowing for either immediate or subsequent use of signal processing techniques. The signals can be recorded in any conventional manner including on magnetic tape or in a computer memory and can be processed into a usable output by printers, plotters, and displays. Thus, in the context of this specification and claims the term means for recording includes any device that converts the microscope output signals into a useable format.

It is also within the scope of the present invention to connect the signal outputs from the microscope to a color television tube. In this configuration the acoustic image can appear superimposed upon the optical image and each image will have a different color.

In addition, it is contemplated that in some applications the microscope can be moved with respect to the object. In that case, the X-Y translator 60 in FIG. 1 moves the entire microscope in a raster pattern and the object being scanned is held stationary. The oscilloscopes 42, 58 are driven in the same manner and the optical and acoustic images are unchanged. Thus, the present invention is understood to include all relative motion between the microscope and the object being scanned.

Further, it should be appreciated that although a laser 8, FIG. 1, and a collimated light source 8, FIG. 5, are shown and described, these light sources are disclosed as preferred embodiments and are not intended to limit the scope of the invention. For example, the present invention also contemplates the use of uncollimated light from an incandescent source.

Thus, although the best modes contemplated for carrying out the present invention have been herein shown and described, it will be apparent in view of the foregoing that modification and variation may be made without departing from what is regarded to be the subject matter of the invention.

What is claimed is:
1. A microscope for scanning an object with light and acoustic waves, comprising:
   a. optical lens means for focusing light on an object located at the optical focal plane of said lens so that the light passes through the object and is modulated thereby;
   b. photodectector means for converting the modulated light into a corresponding electrical signal;
   c. optical lens means located between the optical focal plane and the photodetector means for receiving the light modulated by the object and directing the light onto the photodetector means;
   d. means connected to the photodetector means for recording the electrical signal corresponding to the light modulated by the object;
   e. means for generating acoustic waves;
   f. means connected to the acoustic wave generating means for propagating the acoustic waves therefrom;
   g. acoustic lens means connected to the acoustic wave propagating means for focusing the acoustic waves on the object located at the acoustic focal plane of said lens so that the acoustive waves pass through the object and are modulated thereby;
   h. transducer means for converting the modulated acoustic waves into a corresponding electrical signal;
   i. means located between the acoustic focal plane and the transducer means for propagating the acoustic waves modulated by the object to the transducer means;
   j. means connected to the transducer means for recording the electrical signal corresponding to the acoustic waves modulated by the object; and
   k. means providing relative movement between the object and the acoustic and optical focal planes so that the object is scanned by the light and acoustic waves.

2. The apparatus of claim 1 wherein the optical focal plane and the acoustic focal plane are substantially coincident.

3. The apparatus of claim 1 wherein said propagating means also transmits light waves and further includes means for reflecting the light onto the acoustic focal plane of the microscope.

4. The apparatus of claim 1 wherein the acoustic waves propagate in both the optical lens focusing means and the optical lens receiving means and both said lens means further include means for reflecting the acoustic waves onto the optical focal plane of the microscope.

5. The apparatus of claim 1 wherein the acoustic waves propagate in both the optical lens focusing means and the optical lens receiving means and the axis of propagation of the acoustic waves in each optical lens means is coaxial with the axis of propagating of the light.

6. The apparatus of claim 1 further including an optical beam splitter located on the microscope between the optical receiving lens means and the photodetector means so that a portion of the modulated light is reflected out of the microscope for direct observation of the object.

7. The apparatus of claim 1 wherein both the light and the acoustic wave recording means include cathode ray tubes each having a raster scan and wherein the moving means translates the object in a raster pattern synchronized to the raster scans of the cathode ray tubes.

8. The apparatus of claim 1 wherein the moving means translates the object with respect to the microscope.

9. The apparatus of claim 1 wherein the moving means translates the microscope with respect to the object.

10. A microscope for scanning an object with light and acoustic waves, comprising:
   a. optical lens means for focusing light on an object located at the optical focal plane of said lens so that the light is reflected by the object and is modulated thereby;
   b. photodetector means for converting the modulated light into a corresponding electrical signal, said modulated light being reflected back through the optical lens means and is incident on the photodetector means;
   c. means connected to the photodetector means for recording the electrical signal corresponding to the light modulated by the object;
   d. means for generating acoustic waves;
   e. means connected to the acoustic wave generating means for propagating the acoustic waves therefrom;
   f. acoustic lens means connected to the acoustic wave propagating means for focusing the acoustic waves on the object located at the acoustic focal point of said lens so that the acoustic waves are reflected by the object and are modulated thereby;
   g. transducer means for converting the modulated acoustic waves into a corresponding electrical signal, said acoustic waves being reflected back through the acoustic wave propagating means and are incident on the transducer means;
   h. means connected to the transducer means for recording the electrical signal corresponding to the acoustic waves modulated by the object; and
   i. means providing relative movement between the object and the acoustic and optical focal planes so that the object is scanned by the light and acoustic waves.

11. The apparatus of claim 10 wherein the optical focal plane and the acoustic focal plane are substantially coincident.

12. The apparatus of claim 10 wherein the light propagates in the acoustic wave propagating means and the acoustic wave propagating means further includes means for reflecting the light from the optical lens means onto the acoustic focal plane of the microscope.

13. The apparatus of claim 10 wherein the acoustic waves propagate in the optical lens means and the optical lens means includes means for reflecting the acoustic waves onto the optical focal plane of the microscope.

14. The apparatus of claim 10 wherein the acoustic waves propagate in both the optical lens focusing means and the optical lens receiving means and the axis of propagation of the acoustic waves in each optical lens means is coaxial with the axis of propagation of the light.

15. The apparatus of claim 10 further including an optical beam splitter located on the microscope between the optical lens means and the photodetector means so that a portion of the modulated light is reflected out of the microscope for direct observation.

16. The apparatus of claim 10 wherein both the light and the acoustic wave recording means include cathode ray tubes each having a raster scan and wherein the moving means translates the object in a raster pattern synchronized to the raster scans of the cathode ray tubes.

17. The apparatus of claim 10 wherein the moving means translates the object with respect to the microscope.

18. The apparatus of claim 10 wherein the moving means translates the microscope with respect to the object.

19. A microscope for scanning an object with light and acoustic waves, comprising:
   a. optical lens means for focusing light on an object located at the optical focal plane of said lens so that the light passes through the object and is modulated thereby;
   b. photodetector means for converting the modulated light into a corresponding electrical signal;
   c. optical lens means located between the optical focal plane and the photodetector means for receiving the light modulated by the object and directing the light onto the photodetector means;
   d. means connected to the photodetector means for recording the electrical signal corresponding to the light modulated by the object;
   e. means for generating acoustic waves;
   f. means connected to the acoustic wave generating means for propagating the acoustic waves therefrom;
   g. acoustic lens means connected to the acoustic wave propagating means for focusing the acoustic waves on the object located at the acoustic focal plane of said lens so that the acoustic waves are reflected by the object and are modulated thereby;
   h. transducer means for converting the modulated acoustic waves into a corresponding electrical signal, said acoustic waves being reflected back through the acoustic wave propagating means and are incident on the transducer means;
   i. means connected to the transducer means for recording the electrical signal corresponding to the acoustic waves modulated by the object; and
   j. means providing relative movement between the object and the acoustic and optical focal planes so that the object is scanned by the light and acoustic waves.

20. The apparatus of claim 19 wherein the optical focal plane and the acoustic focal plane are substantially coincident.

21. The apparatus of claim 19 wherein both the light and the acoustic wave recording means include cathode ray tubes each having a raster scan and wherein moving means translates the object in a raster pattern synchronized to the raster scans of the cathode ray tubes.

22. A microscope for scanning an object with light and acoustic waves, comprising:
   a. optical lens means for focusing light on an object located at the optical focal plane of said lens so that the light is reflected by the object and is modulated thereby;
   b. photodetector means for converting the modulated light into a corresponding electrical signal, said modulated light being reflected back through the optical lens means and is incident on the photodetector means;
   c. means connected to the photodetector means for recording the electrical signal corresponding to the light modulated by the object;
   d. means for generating acoustic waves;

e. means connected to the acoustic wave generating means for propagating the acoustic waves therefrom;
f. acoustic lens means connected to the acoustic wave propagating means for focusing the acoustic waves on the object located at the acoustic focal plane of said lens so that the acoustic waves pass through the object and are modulated thereby;
g. transducer means for converting the modulated acoustic waves into a corresponding electrical signal;
h. means located between the acoustic focal plane and the transducer means for propagating the acoustic waves modulated by the object to the transducer means;
i. means connected to the transducer means for recording the electrical signal corresponding to the acoustic waves modulated by the object; and
j. means providing relative movement between the object and the acoustic and optical focal planes so that the object is scanned by the light and acoustic waves.

23. The apparatus of claim 22 wherein the optical focal plane and the acoustic focal plane are substantially coincident.

24. The apparatus of claim 22 wherein both the light and the acoustic wave recording means include cathode ray tubes each having a raster scan and wherein the moving means translates the object in a raster pattern synchronized to the raster scans of the cathode ray tubes.

25. Apparatus for focusing both light and acoustic waves onto the same focal plane, comprising:
a. first means for propagating both light and acoustic waves;
b. first acoustic lens means at one end of the first propagating means for focusing acoustic waves propagating therein onto the focal plane;
c. first optical lens means on the propagating means for focusing light onto the same focal plane; and
d. first means within the propagating means for passing acoustic waves onto the focal plane and for reflecting the light from the optical lens means onto the focal plane.

26. The apparatus of claim 25 further including:
a. second means for propagating both light and acoustic waves;
b. second acoustic lens means at the one end of the second propagating means having a coincident focus with the first acoustic lens means, said second acoustic lens means refracts the acoustic waves after focusing into a substantially parallel beam of acoustic waves propagating in the second propagating means; and
c. second means within the propagating means for passing acoustic waves and for reflecting the light from the focal plane out of the propagating means.

27. Apparatus for focusing both light and acoustic waves on the same focal plane, comprising:
a. first means for propagating both light and acoustic waves;
b. first acoustic lens means at one end of the first propagating means for focusing acoustic waves propagating therein onto the focal plane;
c. first optical lens means on the propagating means for focusing light onto the same focal plane; and
d. first means within the propagating means for passing the light onto the focal plane and for reflecting the acoustic waves onto the focal plane.

28. The apparatus of claim 27 further including:
a. second means for propagating both light and acoustic waves;
b. second acoustic lens means at one end of the second propagating means having a coincident focus with the first acoustic lens means, said second acoustic lens means refracts the acoustic waves after focusing into a substantially parallel beam of acoustic waves propagating in the second propagating means; and
c. second means within the propagating means for passing light and for reflecting the acoustic waves from the focal plane out of the propagating means.

29. Apparatus for focusing both light and acoustic waves onto the same focal plane, comprising:
a. first means for propagating both light and acoustic waves;
b. first acoustic lens means at one end of the first propagating means for focusing acoustic waves propagating therein onto the focal plane; and
c. first optical lens means on the propagating means for focusing light onto the same focal plane, both said light and said acoustic waves have coaxial axes of propagation within the first propagating means.

30. The apparatus of claim 29 further including:
a. second means for propagating both light and acoustic waves;
b. second acoustic lens means at the one end of the second propagating means having a coincident focus with the first acoustic lens means, said second acoustic lens means refracts the acoustic waves after focusing into a substantially parallel beam of acoustic waves propagating in the second propagating means; and
c. second optical lens means on the second propagating means having a coincident focus with the first optical lens means.

31. A method of simultaneously optically and acoustically scanning an object with a microscope comprising the steps of:
a. propagating acoustic waves in an acoustic wave propagating medium;
b. focusing the acoustic waves on an object located at the focal plane of the microscope;
c. modulating the acoustic waves with the object;
d. moving the object, relatively, in a raster pattern;
e. displaying an image having a raster scan synchronized with the raster motion pattern of the object and corresponding to the acoustic waves modulated by the object;
f. focusing light on the object located at the focal plane of the microscope;
g. modulating the light with the object; and
h. displaying an image having a raster scan synchronized with the raster motion pattern of the object and corresponding to the light modulated by the object.

32. The method of claim 31 further including the step of focusing the collimated light on the same point on the object as the acoustic waves are focused upon.

33. The method of claim 31 further including the step of coextensively propagating the light in the same medium as the acoustic waves.

* * * * *